United States Patent
Kobilka et al.

(10) Patent No.: US 12,304,978 B2
(45) Date of Patent: May 20, 2025

(54) BIOBASED MATERIALS DERIVED FROM CYCLIC MONOTERPENES

(71) Applicant: International Business Machines Corporation, Armonk, NY (US)

(72) Inventors: Brandon M. Kobilka, Fishkill, NY (US); Jason T. Wertz, Pleasant Valley, NY (US); Sarah K. Czaplewski-Campbell, Rochester, MN (US); Eric J. Campbell, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 484 days.

(21) Appl. No.: 17/805,708

(22) Filed: Jun. 7, 2022

(65) Prior Publication Data

US 2023/0391904 A1    Dec. 7, 2023

(51) Int. Cl.
| | |
|---|---|
| C08F 134/02 | (2006.01) |
| C01B 19/00 | (2006.01) |
| C01G 45/1214 | (2025.01) |
| C07B 33/00 | (2006.01) |
| C07C 13/00 | (2006.01) |
| C07C 13/20 | (2006.01) |
| C07C 49/543 | (2006.01) |

(52) U.S. Cl.
CPC ........ *C08F 134/02* (2013.01); *C01G 45/1214* (2013.01); *C07C 49/543* (2013.01); *C01B 19/004* (2013.01); *C07B 33/00* (2013.01); *C07C 13/00* (2013.01); *C07C 13/20* (2013.01)

(58) Field of Classification Search
CPC .................................................. C08F 134/02
USPC ................................................ 549/200–299
See application file for complete search history.

(56) References Cited

U.S. PATENT DOCUMENTS

| | | |
|---|---|---|
| 4,564,718 A | 1/1986 | Still et al. |
| 5,723,709 A | 3/1998 | Phillips, Jr. |
| 8,685,207 B2 | 4/2014 | Song et al. |
| 8,969,484 B2 | 3/2015 | Stokes et al. |
| 9,012,385 B2 | 4/2015 | Di Biase et al. |

FOREIGN PATENT DOCUMENTS

| | | |
|---|---|---|
| DE | 10051136 A1 | 4/2002 |
| DE | 102013208386 A1 | 11/2014 |
| GB | 2147909 B | 9/1986 |
| WO | 0279180 W | 10/2002 |

OTHER PUBLICATIONS

Arne Stamm, Pinene-Based Oxidative Synthetic Toolbox for Scalable Polyester Synthesis, Oct. 7, 2021, JACS Au, vol. 1(11), 1949-1960 (Year: 2021).*
Farhat et al., "Biocatalysis for terpene-based polymers," Open Access Published by De Gruyter, https://www.degruyter.com/document/doi/10.1515/znc-2018-0199/html, Feb. 21, 2019, 18 pgs.
Lowe et al., "Functional biorenewable polyesters from carvone-derived lactones," Polym. Chem., 2011,2, 702-708.
Parrino et al., "Polymers of Limonene Oxide and Carbon Dioxide: Polycarbonates of the Solar Economy," https://doi.org/10.1021/acsomega.8b00644, CS Omega 2018, 3, 5, 4884-4890, Publication Date: May 3, 2018, 7 pgs.
Quilter et al., "Polymerisation of a terpene-derived lactone: a bio-based alternative to ε-caprolactone," DOI: 10.1039/C6PY02033J (Communication) Polym. Chem., 2017, 8, 833-837.
Rice, "Bottlebrush Polymers for Functional Materials," https://verduzcolab.blogs.rice.edu/bottlebrush-polymers-for-functional-materials/, printed Apr. 6, 2022, 6 pgs.
Stockmann et al., "Biobased chiral semi-crystalline or amorphous high-performance polyamides and their scalable stereoselective synthesis," Article, Open Access,Published: Jan. 24, 2020, 12 pgs.
Wu et al., "Synthesis of Bottlebrush Polymers with V-Shaped Side Chains," DOI: 10.1016/J.POLYMER.2018.02.001, printed Apr. 6, 2022, 27 pgs.
Zhang et al., "Catalytic Polymerization of a Cyclic Ester Derived from a "Cool" Natural Precursor," Biomacromolecules 2005, 6, 4, 2091-2095, Publication Date:Apr. 23, 2005.

* cited by examiner

*Primary Examiner* — Margaret G Moore
*Assistant Examiner* — James E. Abbott
(74) *Attorney, Agent, or Firm* — Kelsey Skodje

(57) ABSTRACT

A process, a composition, and an article of manufacture are disclosed. The process includes generating a cyclic monoterpene derivative. The generating includes oxidizing a cyclic monoterpene to generate a ketone derivative and oxidizing the ketone derivative to form a lactone derivative. The composition and the article of manufacture include a polymer having monomer repeat units derived from a lactone derivative of a cyclic monoterpene.

20 Claims, 6 Drawing Sheets

BIOBASED MATERIALS DERIVED FROM CYCLIC MONOTERPENES

BACKGROUND

The present disclosure relates to biobased materials and more specifically to compounds derived from cyclic monoterpenes.

Biobased molecular compounds can be obtained from renewable sources, such as plants, and can be used in applications that previously required petroleum-based raw materials. For example, biobased compounds can be building blocks for materials such as plastics, adhesives, pharmaceuticals, etc. Cyclic monoterpenes are examples of biobased compounds that can be obtained from sources such as waste streams of biomass utilizing-processes, turpentine oil, etc.

SUMMARY

Various embodiments of the present disclosure are directed to a process that includes generating a cyclic monoterpene derivative. The generating includes oxidizing a cyclic monoterpene to generate a ketone derivative and oxidizing the ketone derivative to form a lactone derivative.

Additional embodiments of the present disclosure are directed to a composition, which includes a polymer having monomer repeat units derived from a lactone derivative of a cyclic monoterpene. The lactone derivative is formed in a process that includes oxidizing the cyclic monoterpene to generate a ketone derivative and oxidizing the ketone derivative to form the lactone derivative.

Further embodiments of the present disclosure are directed to an article of manufacture that includes a polymer. The polymer has monomer repeat units derived from a lactone derivative of a cyclic monoterpene. The lactone derivative is formed in a process that includes oxidizing the cyclic monoterpene to generate a ketone derivative and oxidizing the ketone derivative to form the lactone derivative.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure

Figure 1:
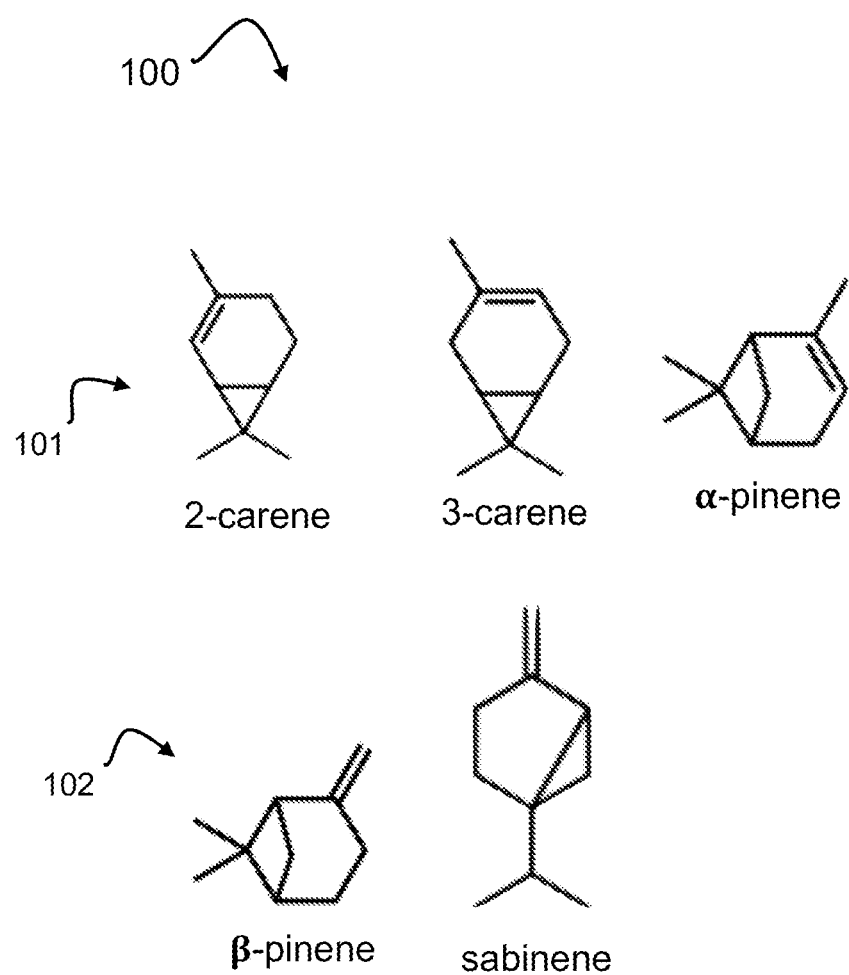
FIG. 1 is a chemical structure diagram illustrating examples of cyclic monoterpenes that may be used to form biobased materials, according to some embodiments of the present disclosure.

While the invention is amenable to various modifications and alternative forms, specifics thereof have been shown by way of example in the drawings, and will be described in detail. It should be understood, however, that the intention is not to limit the invention to the particular embodiments described. Instead, the intention is to cover all modifications, equivalents, and alternatives falling within the spirit and scope of the invention.

DETAILED DESCRIPTION

Embodiments of the present disclosure are generally directed to biobased materials and, more specifically, to materials derived from cyclic monoterpenes. While the present disclosure is not necessarily limited to such applications, various aspects of the disclosure may be appreciated through a discussion of examples using this context.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the articles "a" and "an" preceding an element or component are intended to be nonrestrictive regarding the number of instances (i.e., occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

Unless otherwise noted, ranges (e.g., time, concentration, temperature, etc.) indicated herein include both endpoints and all numbers between the endpoints. Unless specified otherwise, the use of a tilde (~) or terms such as "about," "substantially," "approximately," "slightly less than," and variations thereof are intended to include the degree of error associated with measurement of the particular quantity based upon the equipment available at the time of filing the application. For example, "about" can include a range of ±8%, ±5%, or ±2% of a given value, range of values, or endpoints of one or more ranges of values. Unless otherwise indicated, the use of terms such as these in connection with a range applies to both ends of the range (e.g., "approximately 1 g-5 g" should be interpreted as "approximately 1 g-approximately 5 g") and, in connection with a list of ranges, applies to each range in the list (e.g., "about 1 g-5 g, 5 g-10 g, etc." should be interpreted as "about 1 g-about 5 g, about 5 g-about 10 g, etc.").

Turning now to an overview of technologies relevant to aspects of the present disclosure, in general, biobased compounds include compounds that are isolated or derived from renewable, biological sources, such as plants, fungi, microorganisms, animal products, and atmospheric gases. Biobased compounds are increasingly being used in the syntheses of substances that previously required petroleum-based raw materials. Biobased compounds have applications in sustainable, or "green," materials because they are obtained from renewable sources. Due to the rising costs of fossil fuels and increasing environmental regulatory controls, there is a growing interest in obtaining materials from renewable sources.

Biobased materials can include biobased polymers, composites of biobased polymers and petroleum-based polymers, polymers blended with biobased additives, fillers, etc. Biobased polymers may be synthesized, at least in part, from biobased starting materials (e.g., monomers, crosslinkers, chain-extenders, sidechain functionalizing species, etc.). Biobased materials may include polymers that are entirely biobased or produced from a combination of bio- and petroleum-based monomers.

Embodiments of the present disclosure may provide versatile materials with biobased content. For example, disclosed herein are synthetic pathways for functionalizing and polymerizing cyclic monoterpenes. Functionalization of the cyclic monoterpenes may be used to generate biobased compounds such as small molecules or monomers, oligomers, and/or polymers. The biobased polymers or oligomers have sidechains that can bind reactive species such as flame retardants, plasticizers, colorants, crosslinkers. The biobased compounds may be building blocks for plastics, adhesives, pharmaceuticals, etc.

FIG. 1 is a chemical structure diagram illustrating examples of cyclic monoterpenes 100 that may be used to form biobased materials, according to some embodiments of the present disclosure. Cyclic monoterpenes include two isoprene units and have a chemical formula of $C_{10}H_{16}$. Cyclic monoterpenes can be obtained from sources such as waste streams of biomass utilizing-processes, turpentine oil, plant resins, etc. In some embodiments, turpentine oil is obtained as a byproduct of the cellulose industry, extracted from conifers, etc. The illustrated examples of cyclic monoterpenes include endocyclic alkenes (2-carene, 3-carene, and α-pinene), which are also referred to herein as "monoterpenes 101" or "endocyclic monoterpenes", and exocyclic alkenes (sabinene and β-pinene) 102 which are also referred to herein as "monoterpenes 102" or "exocyclic monoterpenes". The cyclic monoterpenes 100 shown in FIG. 1 are illustrative examples, but any appropriate mono- or bicyclic monoterpenes may be used (e.g., limonene, thujene, camphene, etc.), as will be understood by persons of ordinary skill in the art.

Figure 2:
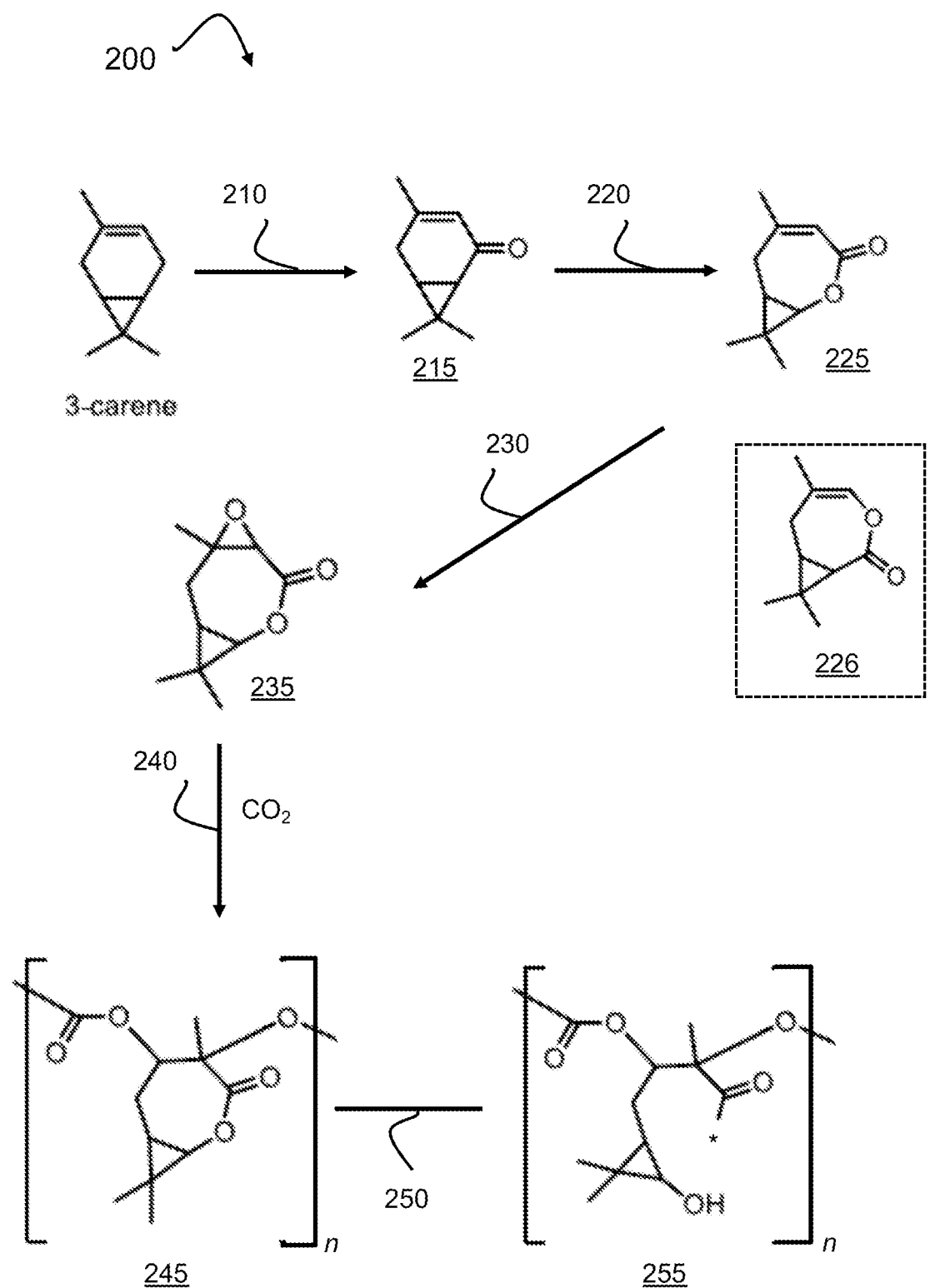
FIG. 2 is a chemical reaction diagram illustrating a process of forming a polymer derived from an endocyclic monoterpene, according to some embodiments of the present disclosure.

FIG. 2 is a chemical reaction diagram illustrating a process 200 of forming a polymer derived from an endocyclic monoterpene, according to some embodiments of the present disclosure. The illustrated endocyclic monoterpene is 3-carene, but substantially the same or similar reaction steps may be carried out with other endocyclic monoterpenes (e.g., monoterpenes 101) to form analogous derivatives. Process 200 includes three oxidation steps 210, 220, and 230. At operation 210, a 3-carene derivative 215 with a ketone moiety is generated. This derivative 215 is referred to herein as "ketone 215". In some embodiments, operation 210 includes forming ketone 215 by oxidizing 3-carene with potassium permanganate ($KMnO_4$) in, for example, an acetone solution. In other embodiments, operation 210 includes forming ketone 215 by oxidizing 3-carene with chromium trioxide ($CrO_3$) in, for example, pyridine. In further embodiments, ketone 215 may be formed by reacting 3-carene with dichlorotetrakis(pyridine)cobalt and oxygen.

At operation 220, ketone 215 is oxidized to form a derivative 225 with a lactone moiety. This derivative 225 is referred to herein as "lactone 225". In some embodiments, reaction conditions may be adjusted using known techniques to produce lactone derivative 226 instead of 225. Derivative 226 may be used in substantially the same reactions (e.g., operations 230-250) as lactone 225 to generate analogous derivatives and polymers. Operation 220 includes forming lactone 225 by reacting ketone 215 with an oxidizing agent such as trifluoroperacetic acid ($CF_3COOOH$). For example, ketone 215 may be mixed with trifluoroperacetic acid in a dichloromethane solution and reacted at about 5° C. to generate lactone 225. In other embodiments, operation 220 includes forming lactone 225 by reacting ketone 215 with meta-chloroperoxybenzoic acid (mCPBA) in chloroform or another suitable organic solvent.

At operation 230, the endocyclic alkene moiety of lactone 225 is oxidized to generate a derivative 235 having an epoxy moiety, which is referred to herein as "epoxy 235". Any appropriate epoxidation reaction conditions can be used. For example, lactone 225 can be reacted with hydrogen peroxide ($H_2O_2$), trifluoracetic acid (TFA), and 1,2-diphenyl-1,2-ethylenediamine (DPEN).

At operation 240, a polycarbonate having n lactone repeat units ("lactone polycarbonate 245") is formed, where n is an integer greater than 1. Operation 240 can include a ring-opening copolymerization (ROCOP) of epoxide 235 and carbon dioxide ($CO_2$). The polymerization uses a catalyst (not shown) such as a β-diiminate (BDI) Zn(II) catalyst (e.g., a BDI-Zn-acetate complex) or other catalyst(s) for epoxide/$CO_2$ ROCOP reactions known to those of ordinary skill in the art.

At operation 250, lactone polycarbonate 245 can be reacted further to generate a polymer ("polycarbonate A 255") having more than one reactive functional group ("reactive site") per repeat unit. In subsequent operations (see below), various materials can be generated by binding sidechain substituents at one or both reactive sites. The illustrated reaction is an example of a lactone ring-opening reaction that can result in the two reactive sites at operation 250. One of the reactive sites on polycarbonate A 255 is at the hydroxyl group. The second reactive site is a functional group bound to polycarbonate A 255 at the starred bond, as shown in FIG. 2. The functional group of the second reactive site can be varied by selection of reactants used in operation 250.

In some embodiments, the second reactive site functional group can be a carboxylic acid (*=—OH), ester (*=—OR, where R is an organic moiety), or carboxamide (*=—NRR', where R is an organic substituent, and R' is a hydrogen atom or a second organic substituent). In order to generate the carboxylic acid reactive site on polycarbonate A 255, lactone polycarbonate 245 can be reacted with an acid or base and water at operation 250. In order to generate the ester reactive site on polycarbonate A 255, lactone polycarbonate 245 can be reacted with an acid or base and an alcohol (ROH) at operation 250. In order to generate the carboxamide reactive site on polycarbonate A 255, lactone polycarbonate 245 can be reacted with an amine ($H_2NR$ or HNRR') and a coupling agent such as dicyclohexyl carbodiimide (DCC) at operation 250.

Figure 3:
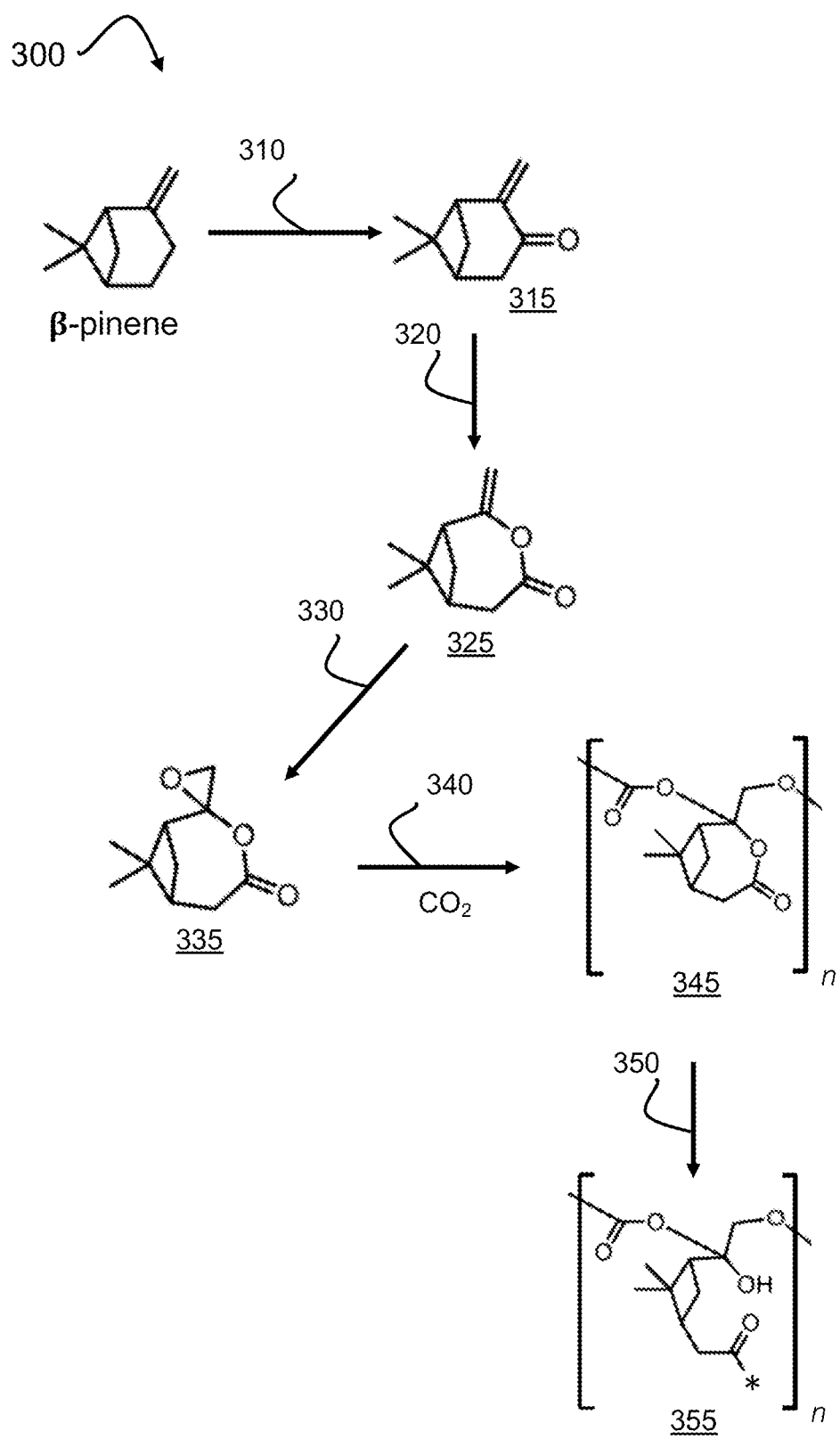
FIG. 3 is a chemical reaction diagram illustrating a process of forming a polymer derived from an exocyclic monoterpene, according to some embodiments of the present disclosure.

FIG. 3 is a chemical reaction diagram illustrating a process 300 of forming a polymer derived from an exocyclic monoterpene, according to some embodiments of the present disclosure. The illustrated exocyclic monoterpene is β-pinene, but substantially the same or similar reaction steps may be carried out with other exocyclic monoterpenes (e.g., monoterpenes 102). At operation 310, a β-pinene derivative 315 with a ketone moiety is generated. This derivative 315 is referred to herein as "ketone 315". In some embodiments, operation 310 includes forming ketone 315 by oxidizing β-pinene with selenium dioxide ($SeO_2$) in, for example, a dichloromethane solution.

At operation 320, ketone 315 is oxidized to form an exocyclic alkene derivative 325 with a lactone moiety. This derivative 325 is referred to herein as "lactone 325". In some embodiments, operation 320 includes forming lactone 325 by oxidizing ketone 315 with a monooxygenase enzyme (e.g., in an ethanol solution).

At operation 330, the exocyclic alkene moiety of lactone 325 is oxidized to generate a derivative 335 having an epoxide moiety, which is referred to herein as "epoxy 335". Any appropriate epoxidation reaction conditions can be used to form epoxy 335. For example, lactone 325 can be oxidized with mCPBA (e.g., in chloroform) or with trifluoroperacetic acid (e.g., in dichloromethane at about 5° C.) at operation 330.

At operation 340, a polycarbonate having n lactone repeat units ("lactone polycarbonate 345") is formed, where n is an integer greater than 1. Operation 340 can include a ring-opening copolymerization (ROCOP) of epoxy 335 and carbon dioxide ($CO_2$). The polymerization uses a catalyst (not shown) such as a β-diiminate (BDI) Zn(II) catalyst (e.g., a BDI-Zn-acetate complex) or other catalyst(s) for epoxide/CO 2 ROCOP reactions known to those of ordinary skill in the art.

At operation 350, lactone polycarbonate 345 can be reacted further to generate a polymer ("polycarbonate B 355") having more than one reactive functional group ("reactive site") per repeat unit. In subsequent operations (see below), various materials can be generated by binding sidechain substituents at one or both reactive sites. The illustrated reaction is an example of a lactone ring-opening reaction that can result in the two reactive sites at operation 350. One of the reactive sites on polycarbonate B 355 is at the hydroxyl group. The second reactive site is a functional group bound to polycarbonate B 355 at the starred bond, as shown in FIG. 3. The functional group of the second reactive site can be varied by selection of reactants used in operation 350.

In some embodiments, the second reactive site functional group can be a carboxylic acid (*═—OH), ester (*═—OR, where R is an organic moiety), or carboxamide (*═—NRR', where R is an organic substituent, and R' is a hydrogen atom or a second organic substituent). In order to generate the carboxylic acid reactive site on polycarbonate B 355, lactone polycarbonate 345 can be reacted with an acid or base and water at operation 350. In order to generate the ester reactive site on polycarbonate B 355, lactone polycarbonate 345 can be reacted with an acid or base and an alcohol (ROH) at operation 350. In order to generate the carboxamide reactive site on polycarbonate B 355, lactone polycarbonate 345 can be reacted with an amine ($H_2NR$ or HNRR') and a coupling agent such as dicyclohexyl carbodiimide (DCC) at operation 350.

Figure 4:
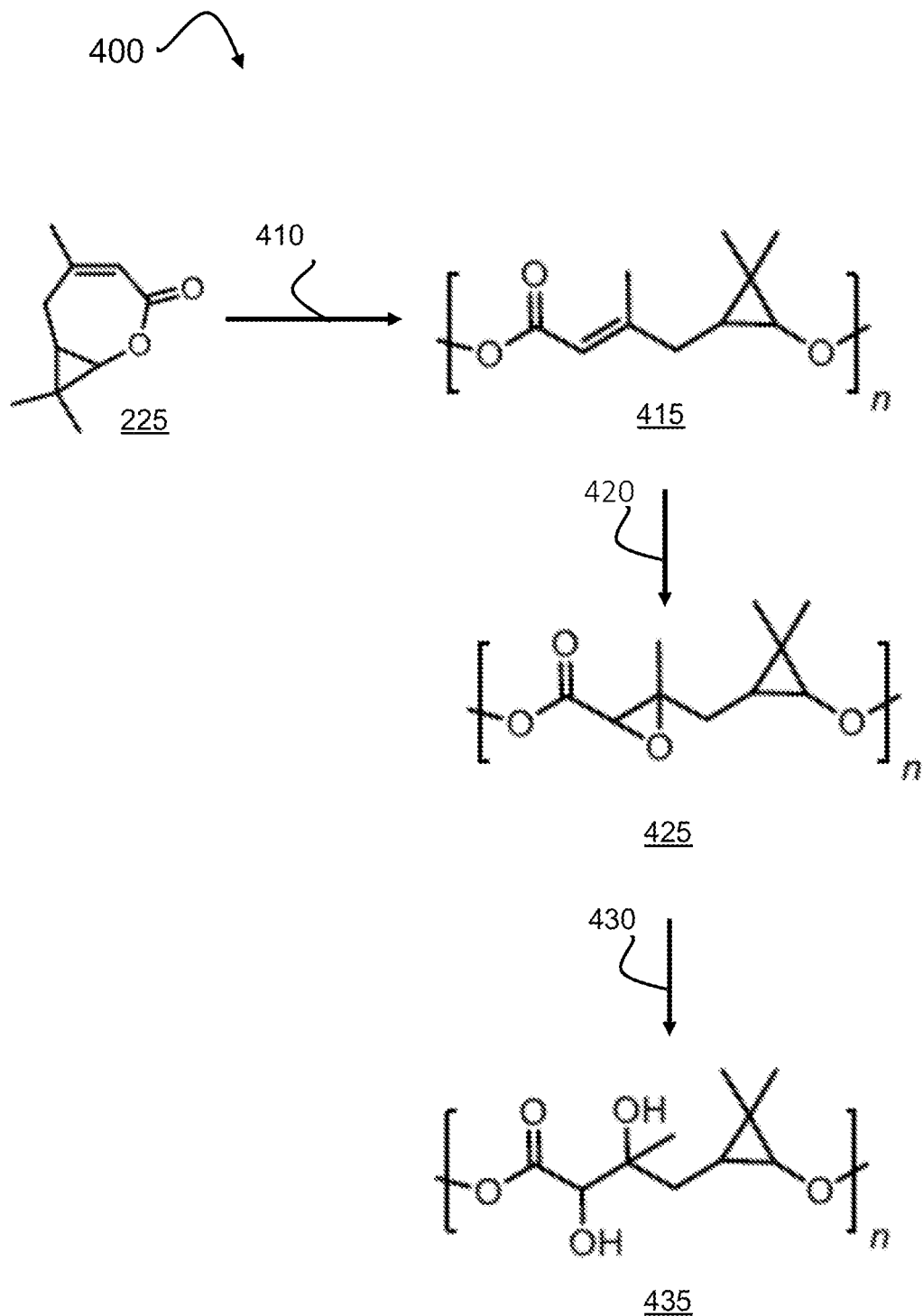
FIG. 4 is a chemical reaction diagram illustrating a process of forming polyesters from cyclic monoterpenes, according to some embodiments of the present disclosure.

FIG. 4 is a chemical reaction diagram illustrating a process 400 of forming polyesters from cyclic monoterpenes, according to some embodiments of the present disclosure. Process 400 can begin with an endocyclic monoterpene-derived lactone such as lactone derivative 225. While derivative 225 is illustrated herein, process 400 can be used to generate various polyesters from derivative 226 or other lactone species derived from cyclic monoterpenes (e.g., endocyclic monoterpenes 101). At operation 410, ring-opening polymerization techniques known in the art can be used to polymerize lactone derivative 225, resulting in a polyester 415 with a number n of repeat units derived from the lactone derivative 225. In some embodiments, a zinc catalyst [Zn] can be used to generate the polyester 415, but any appropriate reactants for ring-opening polymerization of cyclic esters may be used. At operation 420, the alkene moieties on polyester 415 are epoxidized using techniques such as those discussed above with respect to operation 230 (FIG. 2) to form an epoxy-functionalized polyester 425. At operation 430, the epoxy moieties of polyester 425 can be reacted using epoxy-ring opening techniques such as those discussed above with respect to operation 240 (FIG. 2), resulting in a polyester 435 with two reactive (hydroxyl) sites per repeat unit n. A variety of functional groups can be attached at these hydroxyl reactive sites to form polymeric materials with a backbone of polyester 435. Similarly, functional groups can be attached at the hydroxyl and/or starred-bond reactive sites of polycarbonates A 255 and B 355 to form polymeric materials with polycarbonate backbones. An example reaction such as this is illustrated in FIG. 5.

Figure 5:
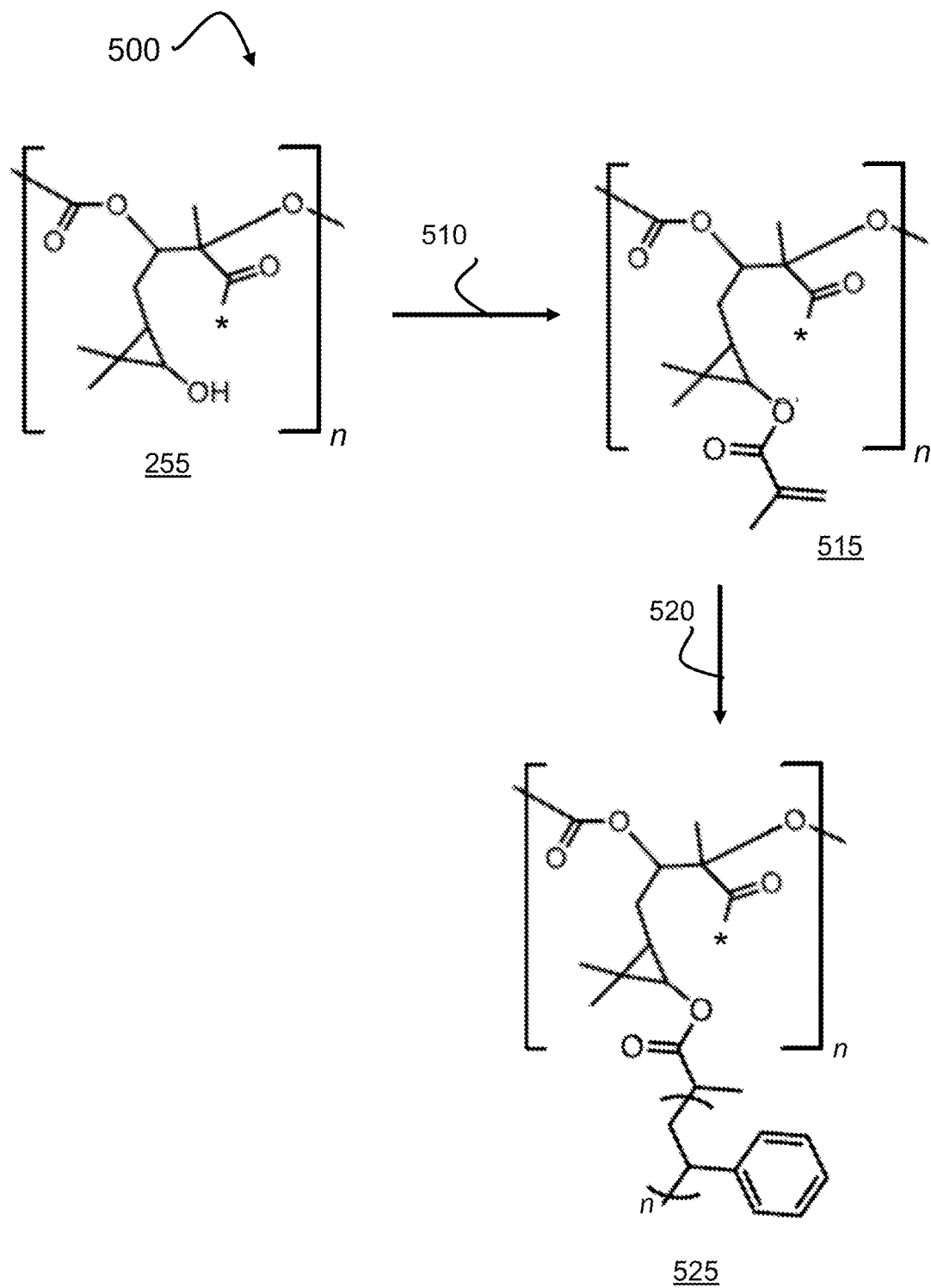
FIG. 5 is a chemical reaction diagram illustrating a process of functionalizing a polycarbonate derived from a cyclic monoterpene, according to some embodiments of the present disclosure.

FIG. 5 is a chemical reaction diagram illustrating a process 500 of functionalizing a polycarbonate derived from a cyclic monoterpene, according to some embodiments of the present disclosure. The illustrated polymer is polycarbonate A 255 (FIG. 2), but substantially similar reactions can be carried out with hydroxyl reactive sites on various polymers herein (e.g., polycarbonate A 255, polycarbonate B 355, polyester 435, and/or analogues thereof). The illustrated example includes reacting hydroxyl groups of polycarbonate A 255 with an acrylate to form esters at operation 510. For example, operation 510 can include reacting polycarbonate A 255 with acryloyl chloride and thionyl chloride.

Various reactions can be carried out to attach other chemical species at the acrylate carbon-carbon double bonds of the resulting acrylate-functionalized polycarbonate 515. Operation 520 illustrates an example of this wherein polystyrene sidechains are formed by reacting the acrylate-functionalized polycarbonate 515 with a radical initiator. The radical initiator and other reaction conditions can be selected based on techniques known in the art for generating polystyrenes from acrylate species. As discussed in greater detail below, the resulting copolymer 525 may be reacted further (e.g., at the second reactive site of the monoterpene-derived polymer repeat units and/or reactive sites on the polystyrene), although these reactions are not illustrated in FIG. 5.

Figure 6:
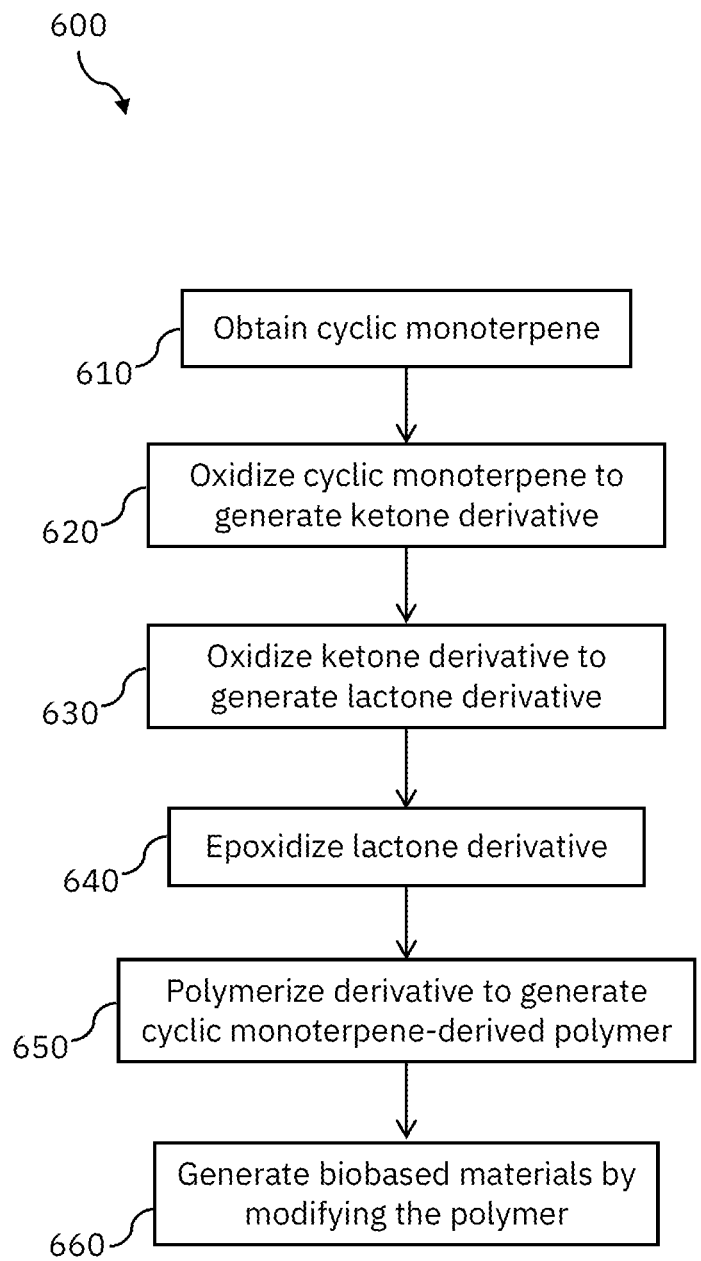
FIG. 6 is a flow diagram illustrating a process of forming cyclic monoterpene-derived polymers, according to some embodiments of the present disclosure.

FIG. 6 is a flow diagram illustrating a process 600 of forming cyclic monoterpene-derived polymers, according to some embodiments of the present disclosure. A cyclic monoterpene can be obtained. This is illustrated at operation 610. For example, endocyclic and/or exocyclic monoterpenes can be extracted from biomass and other renewable/biobased sources. This is discussed in greater detail with respect to FIG. 1. The cyclic monoterpene can then be oxidized to generate a ketone moiety at a carbon atom of the cyclic (ring) portion of the monoterpene. This is illustrated at operation 620. An example oxidation that can be carried out at operation 620 when the cyclic monoterpene is an endocyclic alkene is illustrated in FIG. 2 (operation 210). An example oxidation that can be carried out at operation 620 when the cyclic monoterpene is an exocyclic alkene is illustrated in FIG. 3 (operation 310). Operation 620 results in a ketone derivative (e.g., ketone 215 or ketone 315).

The ketone derivative formed at operation 620 can be oxidized to generate a lactone derivative. This is illustrated at operation 630. An example oxidation that can be carried out at operation 630 when the ketone derivative is an endocyclic alkene is illustrated in FIG. 2 (operation 220). An example oxidation that can be carried out at operation 630 when the ketone derivative is an exocyclic alkene is illustrated in FIG. 3 (operation 320). Operation 630 results in a lactone derivative (e.g., lactone 225 or lactone 325).

In some embodiments, the endocyclic or exocyclic alkene moiety of the lactone derivative formed at operation 630 can be epoxidized. This is illustrated at operation 640. An example epoxidation that can be carried out at operation 640 when the lactone derivative is an endocyclic alkene is illustrated in FIG. 2 (operation 230). An example oxidation that can be carried out at operation 640 when the lactone derivative is an exocyclic alkene is illustrated in FIG. 3 (operation 330). Operation 640 results in an epoxidized lactone derivative (e.g., epoxy 235 or epoxy 335). However, operation 640 may be omitted in some embodiments (see below).

A polymerization reaction can be used to form a cyclic monoterpene-derived polymer. This is illustrated at operation 650. For example, a polycarbonate can be formed by reacting an epoxidized derivative with $CO_2$ and an appropriate catalyst (see, e.g., operation 240 in FIG. 2 or operation 340 in FIG. 3) via ROCOP. Further, a derivative formed at operations 620-640 may be polymerized at operation 650 under appropriate reaction conditions. For example, a lactone derivative formed at operation 630 can be reacted to form a polyester (see e.g., process 400 illustrated in FIG. 4). In other embodiments (not shown), additional modifications/functionalizations can be made to derivatives generated at operations 620, 630, and 640 in order to produce various functionalized monomers that can be polymerized at operation 650. In further embodiments (not shown), small molecules can be generated from these cyclic monoterpene derivatives and, optionally, used in synthetic or other chemical processes that do not include polymerization of the derivatives.

In embodiments that include formation of a cyclic monoterpene-derived polymer, additional reactions and/or other modifications can be made to generate materials having a variety of properties. This is illustrated at operation 660. For example, when a polymer having lactone moieties (e.g., polycarbonate 245 or polycarbonate 345) is generated at operation 650, a ring-opening reaction can be carried out to convert the lactone into reactive sites including a hydroxyl and a second reactive site such as a second hydroxyl, an alcohol, an ester, or an amide. This is discussed in greater detail with respect to FIGS. 2 and 3. In embodiments where polymers having epoxy repeat units are formed (e.g., polyester 425), ring-opening of the epoxies can form polymers with two hydroxyl groups (e.g., polyester 435).

Further, as will be understood by persons of ordinary skill in the art, numerous additional or alternative modifications can be made to the cyclic monoterpene-derived polymers disclosed herein. In some embodiments, various sidechain groups can be bound at one or both reactive sites of polycarbonate A 255, polycarbonate B 355, or polyester 435. For example, reactive flame retardants (e.g., phosphates, phosphonates, phosphinates, etc.) can be added at the hydroxyl reactive site(s). Other sidechain functionalizations that may be added can include plasticizers, colorants, crosslinkers, copolymers, etc.

Crosslinkers and/or chain-extenders may also bind to the polymer reactive sites. Examples of compounds that can be used as crosslinkers or chain-extenders can include ethylene glycol, di- or triethylene glycol, propylene glycol, di- or tripropylene glycol, 1,3-propanediol, 1,3- or 1,4-butanediol, neopenyl glycol, 1,6-hexanediol, 1,4-cyclohexanedimethanol, hydroquinone bis(2-hydroxyethyl) ether, ethanolamine, di- or triethanolamine, methyldiethanolamine, phenyldiethanolamine, glycerol, trimethylolpropane, 1,2,6-hexanetriol, pentaerythritol, N,N,N',N'-tetrakis-(2-hydroxypropyl)ethylenediamine; diethyl-toluenediamine, dimethyl-thio-toluenediamine, etc.

In further embodiments, sidechain small molecules having reactive groups compatible with various polymer platforms can be attached at one or both reactive sites. For example, bromo-methacrylate sidechains can be used in atom transfer radical polymerization (ARTP), siloxane sidechains can be used in silicon-based materials such as polydimethylsiloxane (PDMS), etc.

Similarly, sidechain small molecules having reactive groups compatible with other reactions/modifications can be attached to the cyclic monoterpene-derived polymers. In some embodiments, this can be used to generate bottlebrush polymers having cyclic monoterpene-derived backbones. Additionally, appropriate sidechain reactive groups can participate in click chemistry (e.g., to attach biomolecules). For example, sidechains having azide or alkyne reactive groups may participate in azide-alkyne cycloaddition reactions, and sidechains having alkene (e.g., vinyl) or thiol reactive groups may participate in thiol-ene reactions.

Polymers formed, at least in part, from the disclosed cyclic monoterpenes may be used in applications such as plastics used in electronics hardware (e.g., integrated circuit packages). Additional applications can include acoustic dampening, cushioning, plastics, synthetic fibers, insulation, coatings, bio-adhesives, elastomers, thermoplastics, emulsions, thermosets, etc. Further, materials containing the cyclic monoterpene-derived polymers can be incorporated into various devices with electronic components that can include printed circuit boards (PCBs), semiconductors, transistors, optoelectronics, capacitors, resistors, chip carriers, etc.

It should be noted that, in some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these.

In some embodiments, organic substituents R and R' (e.g., at reactive sites discussed with respect to FIGS. 2 and 3) can be independently selected from cyclic, linear, or branched hydrocarbons, cyclic or acyclic aromatic substituents, or functionalized derivatives thereof and can be any appropriate size (e.g., substituents including one to twelve carbon atoms).

The synthetic processes discussed herein and their accompanying drawings are not to be construed as limiting. One skilled in the art would recognize that a variety of synthetic reactions may be used that vary in reaction conditions, components, methods, etc., which ultimately generate one or both of cyclic monoterpene-derived compounds and their corresponding polymer derivatives. In addition, the reaction conditions can optionally be changed over the course of a process. Further, in some embodiments, processes can be added or omitted while still remaining within the scope of the disclosure, as will be understood by a person of ordinary skill in the art.

What is claimed is:
1. A process, comprising:
  generating a cyclic monoterpene derivative, the generating comprising:

oxidizing a cyclic monoterpene to generate a ketone derivative;
oxidizing the ketone derivative to form a lactone derivative; and
epoxidizing the lactone derivative; and
reacting the epoxidized lactone derivative to form a polycarbonate.

2. The process of claim 1, wherein the cyclic monoterpene is an endocyclic alkene.

3. The process of claim 2, wherein the oxidizing the cyclic monoterpene comprises reacting the cyclic monoterpene with potassium permanganate ($KMnO_4$).

4. The process of claim 1, wherein the cyclic monoterpene is an exocyclic alkene.

5. The process of claim 4, wherein the oxidizing the cyclic monoterpene comprises reacting the cyclic monoterpene with selenium dioxide ($SeO_2$).

6. A composition, comprising:
a polycarbonate comprising monomer repeat units derived from a derivative of a cyclic monoterpene, the derivative generated in a process comprising:
oxidizing a cyclic monoterpene to generate a ketone derivative;
oxidizing the ketone derivative to form a lactone derivative; and
epoxidizing the lactone derivative.

7. The composition of claim 6, wherein a plurality of the monomer repeat units have at least one sidechain functional group.

8. The composition of claim 6, wherein each of the monomer repeat units has two reactive sites.

9. The composition of claim 6, wherein the cyclic monoterpene is an endocyclic alkene.

10. The composition of claim 9, wherein the oxidizing the cyclic monoterpene comprises reacting the cyclic monoterpene with potassium permanganate ($KMnO_4$).

11. The composition of claim 6, wherein the cyclic monoterpene is an exocyclic alkene.

12. The composition of claim 11, wherein the oxidizing the cyclic monoterpene comprises reacting the cyclic monoterpene with selenium dioxide ($SeO_2$).

13. An article of manufacture, comprising:
a polycarbonate comprising monomer repeat units derived from a derivative of a cyclic monoterpene, the derivative generated in a process comprising:
oxidizing a cyclic monoterpene to generate a ketone derivative;
oxidizing the ketone derivative to form a lactone derivative; and
epoxidizing the lactone derivative.

14. The article of manufacture of claim 13, wherein a plurality of the monomer repeat units have at least one sidechain functional group.

15. The article of manufacture of claim 13, wherein each of the monomer repeat units has two reactive sites.

16. The process of claim 1, wherein the reacting the epoxidized lactone derivative to form the polycarbonate comprises a ring-opening copolymerization of the epoxidized lactone derivative with carbon dioxide.

17. The process of claim 1, further comprising generating acrylate reactive groups on the polycarbonate.

18. The process of claim 17, further comprising forming sidechains at the acrylate reactive groups.

19. The composition of claim 9, wherein the oxidizing the cyclic monoterpene comprises reacting the cyclic monoterpene with chromium trioxide ($CrO_3$).

20. The composition of claim 9, wherein the oxidizing the cyclic monoterpene comprises reacting the cyclic monoterpene with dichlorotetrakis(pyridine) cobalt and oxygen.

* * * * *